US005521164A

United States Patent [19]
della Valle et al.

[11] Patent Number: 5,521,164
[45] Date of Patent: May 28, 1996

[54] METHOD FOR THE PREPARATION AND PURIFICATION OF A MIXTURE OF GLYCOSPHINGOLIPIDS FREE FROM CONTAMINATION BY NON-CONVENTIONAL VIRUSES

[75] Inventors: Francesco della Valle; Lanfranco Callegaro; Silvana Lorenzi, all of Padua, Italy

[73] Assignee: Fidia, S.p.A., Abano Terme, Italy

[21] Appl. No.: 116,268

[22] Filed: Sep. 3, 1993

Related U.S. Application Data

[63] Continuation of Ser. No. 721,498, filed as PCT/EP90/01960, filed Nov. 16, 1990, published as WO91/07417, May 30, 1991, abandoned.

[30] Foreign Application Priority Data

Nov. 17, 1989 [IT] Italy .................... 41747/89
Oct. 18, 1990 [IT] Italy .................... 41716/90

[51] Int. Cl.⁶ .................... A61K 35/30; A61K 31/715
[52] U.S. Cl. .................... 514/54; 514/23; 210/633; 536/1.11; 536/53; 536/55.3; 536/124; 536/17.9
[58] Field of Search .................... 536/53, 55.3, 124, 536/1.1; 210/633; 514/23, 54

[56] References Cited

U.S. PATENT DOCUMENTS

| | | | |
|---|---|---|---|
| 3,346,413 | 4/1969 | Okany | 554/21 |
| 4,707,469 | 11/1987 | della Valle et al. | 54/26 |

FOREIGN PATENT DOCUMENTS

| | | |
|---|---|---|
| 0150712 | 8/1985 | European Pat. Off. . |
| 0183572 | 6/1986 | European Pat. Off. . |
| 0319890 | 6/1989 | European Pat. Off. . |
| 60-181019 | 9/1985 | Japan . |
| 61-180719 | 8/1986 | Japan . |
| WO87/01939 | 4/1987 | WIPO . |

OTHER PUBLICATIONS

A. S. Walker et al American Journal of Public Health, vol. 73, No. 6 (Jun. 1983) pp. 661–665.
Commission of the European Communities (Mar. 1990) Ad Hoc Working Party on Biothechology/Pharmacy: Validation of Virus Removal and Inactivation process.
Ariga et al, J. Biol. Chem. 257(5):2230–5 (1982).
S. Ando Neurochemistry Int., vol. 5, No. 5 (1983) pp. 507–537.
L. Svennerholm Journal of Neurochemistry, vol. 10 (1963(pp. 613–623.
P. H. Fishman et al Science, vol. 194 (1976) pp. 906–915.
P. Doherty et al Journ. of Neurochemistry, vol. 44, No. 4 (1985) pp. 1259–1265.
S. D. Skaper et al Molecular Neurobiology, vol. 3 (1989) pp. 173–199.
B. Ceccarelle et al Adv. Exp. Med. Biol., vol. 71 (1976) pp. 275–293.

A. Gorio et al Brain Research, vol. 197 (1980) pp. 236–241.
A. Gorio et al Neuroscience, vol. 8, No. 3 (1983) pp. 417–249.
F. Norido et al Experimental Neurology, vol. 83 (1984) pp. 221–232.
F. DiGregorio et al Cancer Chemother Pharmacol, vol. 26 (1990) pp. 31–36.
A. C. Cuello et al Brain Research, vol. 376 (1986) pp. 373–377.
S. E. Karpaik et al CRC Critical Ref. in Neurobiology, vol. 5, Issue 3 (1990) pp. 221–237.
G. Toffano et al Brain Research, vol. 296 (1984( pp. 233–239.
G. Jonsson et al Developmental Brain Research, vol. 16, (1984) pp. 171–180.
F. Vaccarino et al Proc. Natl. Acad. Sci. USA, vol. 84 (1987) pp. 8707–8711—Neurobiology.
G. Tettamanti et al Biochimica et Biophysica Acta, vol. 296 (1973) pp. 160–170.
E. G. Trams et al Biochimica et Biophysica Acta, vol. 60 (1962) pp. 350–358.
J. R. Wherret et al Trans. Am. Neurol. Assoc., vol. 88 (1963) pp. 108–111 (CA 61:9895d).
CA 61:9851c N. Eldredge et al.
G. A. Wells et al The Veternary Record, vol. 121 (1987) pp. 419–420.
H. Fraser et al Veterinary Record, vol. 123 (1988) p. 472.
J. Hope et al Nature, vol. 336 (1988) pp. 390–392.
J. W. Wilesmith et al The Veterinary Record, vol. 123 (1988) pp. 638–644.
K. L. Morgan The Veterinary Record, vol. 122 (1988) pp. 445–446.
J. Cherfas Science, vol. 267 (1990) p. 523.
I. H. Pattison et al The Veterinary Record, vol. 90, No. 17 (1972) pp. 465–468.
R. M. Barlow et al The Veterinary Record, vol. 126 (1990) pp. 111–112.
G. D. Hunter et al J. gen. Microbiol., vol. 37 (1964) pp. 261–258.
Rosenbert et al Annals of Neurology, vol. 19, No. 1 (1986) pp. 75–77.
P. Brown et al Journal of Infectious Diseases, vol. 153, No. 6 (1986) pp. 1145–1148.
R. H. Kimberlin et al Journal of the Neurobiological Sciences, vol. 59 (1983) pp. 355–369.
Von H. Wiegandt Angewandte Chemie, vol. 80, (1968) pp. 89–98.

(List continued on next page.)

Primary Examiner—Douglas W. Robinson
Assistant Examiner—Kathleen Kahler Fonda
Attorney, Agent, or Firm—Birch, Stewart, Kolasch & Birch

[57] ABSTRACT

The process of the invention relates to a process for the preparation of a ganglioside mixture, free from contaminants associated with non-conventional, life-threatening viruses, without altering the biological and pharmacological characteristics of the mixture on the central and peripheral nervous systems.

18 Claims, 8 Drawing Sheets

OTHER PUBLICATIONS

S. Bogoch et al Brit. J. Pharmacology, vol. 18 (1962) pp. 325–330.

X. Xia CA 104:84884t (1986) p. 337.

V. I. Efremenko et al CA 101:226354j (1984) p. 406.

J. N. Kanfer CA 72:117682b (1970) p. 16.

J. K. Anderson et al CA 88:116832u (1978) p. 186.

H. Kadowaki et al CA 101:226115g (1984) p. 387.

G. Gazzotti et al CA 102:217678m (1985) p. 309.

M. Hiraiwa et al CA 105:205184w (1986) pp. 259–260.M. Caldwell Discover, "Mad Cows and Wild Proteins" (Apr. 1991) pp. 69–94.

Y. Hirabayashi et al Journal of Chromatography, vol. 445 (1988) pp. 377–384.

S. Ando et al Journal of Chromatography, vol. 405 (1987) pp. 125–134.

T. Ariga et al Journal of Lipid Research, vol. 28 (1987) pp. 285–291.

M. C. Byrne et al Analytical Biochemistry, vol. 148 (1985) pp. 163–173.

S. Ladisch et al Analytical Biochemistry, vol. 146 (1985) pp. 220–231.

T. Ariga et al Archives of Biochemistry and Biophysics, vol. 232 No. 1 (1984) pp. 305–309.

T. Ariga et al Journal of Lipid Research, vol. 24 (1983) pp. 737–745.

J. Hagman et al Biochimica et Biophysica Acta, vol. 720 (1982) pp. 181–187.

J. A. J. Randell et al Journal of Chromatography, vol. 195 (1980) pp. 257–264.

L. Svennerholm et al Biochimica et Biophysica Acta, vol. 617 (1980) pp. 97–109.

K. Wantanabe et al Journal of Biological Chemistry, vol. 254 No. 17 (1979) pp. 8223–8229.

N. Kawamura et al Journal of Biochem. vol. 81 (1977) pp. 1217–1225.

T. P. Carter et al Meth. Enzym., vol. 35 (1975) pp. 549–551.

S. Hakomori et al Meth. Enzym., vol. 32 (1974) pp. 345–367.

T. P. Carter et al Lipids, vol. 8, No. 10, pp. 537–548.

G. Tettamanti et al Biochemica et Biophysica Acta, vol. 196 (1973) pp. 160–170.

M. W. Spence Canadian Journal of Biochemistry, vol. 47 (1969) pp. 735–742.

R. Ledeen et al Biological Diagnosis of Brain Disorders (1973) pp. 372–376.

METHOD FOR THE PREPARATION AND PURIFICATION OF A MIXTURE OF GLYCOSPHINGOLIPIDS FREE FROM CONTAMINATION BY NON-CONVENTIONAL VIRUSES

This application is a continuation of application Ser. No. 07/721,498, filed on Sep. 11, 1991, now abandoned.

FIELD OF THE INVENTION

The present invention relates to a process for the preparation of a specific mixture of gangliosides, and the product produced by such process, obtained by a process which selectively eliminates contaminants associated with non-conventional, life-threatening viruses, without altering the biological and pharmacological characteristics of the mixture with regard to its effects on the central and peripheral nervous systems.

BACKGROUND OF THE INVENTION

Gangliosides, glycosphingolipids containing sialic acid, are normal constituents of all cell membranes in mammals and are abundant in the nerve tissue (Ando S.: Neurochem. Int. 5:507, 1983). Four gangliosides, $GM_1$, $GD_{1a}$, $GD_{1b}$ and $GT_{1b}$ (nomenclature according to Svennerholm L., J. Neurochem, 10:613, 1963), constitute 80–90% of the total ganglioside content of the mammal brain. Gangliosides are specifically localized in the outer layer of the plasma membrane, suggesting that they play an important role in many biological activities, for instance as a "sensor" and/or receptor for various molecules, and in the transfer of information through the cell membranes (Fishman et al.: Science 194:906, 1976). They therefore play a key role in the regulation of neuronal development and repair in the central and peripheral nervous systems.

There is indeed ample documentation that gangliosides are able to favorably influence functional recovery following lesion in the peripheral nervous system (PNS) and central nervous system (CNS), by the involvement of specific membrane mechanisms and by interaction with neurotrophic factors as revealed by in vitro studies on neuronal cultures (Doherty P. et al., J. Neurochem. 44:1259, 1985; Skaper S. et al., Molecular Neurobiology, 3:173, 1989).

In particular, it has been reported that the administration of gangliosides in vivo facilitates nerve regeneration and functional recovery in the PNS under pathological conditions: positive effects have been described in models of traumatic neuropathies (Ceccarelli B. et al., Adv. Exp. Med. Biol. 71:275, Plenum Press, New York, 1976; Gorio A. et al., Brain Res. 7:236, 1980; Gario A. et al., Neuroscience 8:417, 1983), metabolic neuropathies (Norido F. et al., Exp. Neurol. 83:221, 1984) and toxic neuropathies (Di Gregorio F. et al., Cancer Chemother., Pharmacol. 26:31, 1990).

With regard to the CNS, positive effects have been widely reported of recovery induced by monosialoganglioside $GM_1$ in models of ischemia (Cuello A. C. et al., Brain Res. 376:373, 1986; Karpiak S. E. et al., CRC Critical Rev. in Neurobiology, Vol. 5, Issue 3, 1990), traumatic lesion (Toffano G. et al., Brain Res. 296:233, 1984) and neuronotoxic lesion (Johnsson J., Dev. Brain Res., 16:171, 1984) in various neuronal systems of different animal species. It has recently been discovered that gangliosides can inhibit the translocation and activation of protein kinase C induced by glutamate (Vaccarino F. et al., Proc. Nat. Acad. Sci. USA, 84:8707, 1987). This action is very important in conditions of ischemic damage, where there have been reports of a crucial role played by excitatory amino acids, such as glutamate, which trigger a cascade of events leading to neuronal death. This mechanism could favor the survival of neurons in the area around the lesion, prevent retrograde degeneration, and accelerate the reparative growth response to local trophic factors.

The results of experimental research have been amply confirmed by those from the clinical use of gangliosides. For over ten years gangliosides have been used as therapeutic agents in almost all forms of peripheral neuropathy, from those forms resulting from mechanical damage to those caused by toxic factors or deficiencies, from infectious and inflammatory disorders to metabolic dysfunctions. These drugs have proved to be equally efficacious in mono and polyneuropathies, in sensory-motor disorders and in pathologies affecting the autonomic nervous system, such as in many neuropathies affecting the cranial nerves, for instance Bell's palsy, trigeminal neuralgia, and neuralgia caused by herpes zoster. Gangliosides, and in particular the monosialoganglioside, can be widely used in all pathologies connected with acute lesions in the CNS of a vascular or traumatic type and in the sequelae of such pathologies (cerebral ischemia, cranial and spinal trauma).

Their proven reparative activity in the CNS also supports their use in chronic neurodegenerative pathologies, such as Parkinson's disease and Alzheimer's disease. The fact that they are "endocoids" (endogenous drugs) by nature, being natural components of the neuronal membranes, explains their excellent tolerability and the absence, even in prolonged treatments with high doses, of side effects which are so frequent in some conventional therapies for peripheral neuropathies.

In general, suitable ganglioside mixtures, for example a formulation of the following kind: $GM_1$ from 18% to 24%, $GD_{1a}$ from 36% to 44%, $GD_{1b}$ from 12% to 18%, $GT_{1b}$ from 16% to 22%, or the single ganglioside fractions, particularly the monosialoganglioside $GM_1$, present biological activities such as those described. These gangliosides, as suitable mixtures or single fractions, in particular the monosialoganglioside $GM_1$, are extracted from mammal brains and it is therefore necessary, given their particular biological function and their therapeutic application previously described with regard to the peripheral and central nervous systems, to utilize purification methods which guarantee a final product which is absolutely pure and free from biological and chemical contaminants.

It has long been known that it is possible to extract, on a research level, mixtures of gangliosides (Tettamanti et al., Biochim. e Biophys. Acta, 296:160, 1973; Trams et al., Biochim. e Biophys. Acta, 60:350, 1962: Bogoch et al., British J. Pharm., 18:625, 1962; Wiegandt et al., Angew Chem. 80:89, 1968; U.S. Pat. No. 3,436,413; and C. A. 61, 9851C, 9895d), but none of the aforesaid methods was developed with a view to demonstrating the elimination and destruction of components associated with non-conventional viruses. One reason for this is that, at the time, such diseases, affecting the mammalian species to which the brains used for extraction belonged, were as yet unknown. Another reason is that no reagents were available for the specific identification of potentially dangerous components, whereas today such reagents have been made available by specific methodologies developed on the basis of newly-acquired knowledge gleaned from the scientific evolution of molecular biology techniques.

Sometimes situations of a pathological type can arise wherein the pathogenic agent or agents cannot be identified.

One such pathological situation is called bovine spongiform encephalopathy (BSE), first reported in England in 1986 (Wells G. et al., Vet. Record, 419, 1986). This name derives from the spongy appearance of the brain tissue from afflicted animals. When sections of tissue are analyzed by microscope, the main lesions are comprised by extensive neuronal vacuoles.

All available evidence points to the fact that BSE belongs to a group of degenerative encephalopathies of the central nervous system which are invariably fatal in outcome and are caused by a group of non-conventional, infectious agents (Fraser et al., Vet. Record 123:472, 1988; Hope et al., Nature 336:390, 1988). This group also includes scrapie of sheep and goats, the chronic emaciating disease which afflicts captive deer, infectious encephalopathy of mink on mink farms, and two human diseases; kuru and Creutzfeldt-Jacob disease. The histopathological lesions caused in the brain by these diseases are similar in all cases and are comparable to those caused by BSE. Many theories have been put forward on the nature of these etiological agents, which are neither bacteria nor virus, are unlike any other known organism and are therefore known as unconventional viruses. On account of their long incubation periods, running from the moment of infection to the onset of symptoms, these viruses are also known as "slow viruses".

Since the few cases observed in 1986, the disease spread and has reached epidemic proportions in Britain, affecting some 14,000 cattle and increasing steadily by about 250–300 cases each week. The infected cattle show no signs of disease for several years (the incubation period being 4–5 years), but once symptoms have appeared the animals rapidly deteriorate and die.

An epidemiological study by the Central Veterinary Laboratory of the British Ministry of Agriculture (Wilesmith et al., Vet. Record. 123:638, 1988) showed the source of infection to be animal fodder made with the processed carcasses of other ruminants, sold in the form of powdered meat or bone. Since the encephalopathy can be transmitted to a wide range of animal species, it seems reasonable to assume that BSE is the result of infection by the etiological agent responsible for scrapie, transmitted from sheep by means of these contaminated foodstuffs (Morgan K L, Vet. Record 122:445, 1988).

On the basis of the results of this study, the British government banned, by an order which came into force on 18th Jul. 1988, the sale and supply of animal foodstuffs containing animal proteins derived from ruminants.

The general opinion is that many factors have contributed together to the sudden appearance of BSE in Britain (Cherfas J., Science, Feb. 1990, 523).

Firstly, the number of sheep in Great Britain increased rapidly in the late 70's and early 80's, and with this the incidence of scrapie, an endemic disease of sheep in Europe for over 250 years (Pattison et al., Vet. Record 90:465, 1972). At the same time, in the wake of the petrol crisis, factories producing animal fodder changed their methods of processing carcasses to a lower-temperature system which was probably less efficient in destroying the highly resistant scrapie agent. All except one of the producers of these foodstuffs abandoned the use of solvents such as benzene, hexane and trichloroethylene, to remove excess fats from soybean and bone meal. Perhaps most significant of all was that the final stage of heating of the products to remove the solvents was consequently left out: indeed this phase required very high temperatures.

Moreover, government policy encouraged breeders to produce more milk, and wean calves early by feeding them protein-rich diets. These animals were often of poor quality, since meal made from meat and bone was cheaper than products made with soybean and fish which are surer sources of protein. Studies to find how the disease is transmitted are fundamental to BSE research. The most important aspect of these experiments is that, by identifying the limits of the inter-species barriers to transmission of the pathogenic agent, it is possible to assess the risk of BSE infection to any one species. Fraser et al. (Vet. Record, 123:472, 1988) demonstrated that the disease could be passed from cattle to mice. They inoculated extracts from the brains of cattle which had died from BSE into the brains of mice which subsequently developed the disease. Later, Barlow et al. (Vet. Record, 3 Feb. 1990) transmitted the disease to mice by feeding them infected brains. It was the first proof that BSE could be contracted by eating infected material. No other tissue from afflicted animals (spleen, spinal cord, lymphatic tissues, milk etc.) was able to produce the disease in mice.

There is proof that scrapie can be transmitted to lambs by their mothers, but so far no evidence has come to light of possible vertical or horizontal transmission of the etiological agent of BSE in cattle.

The agents which cause subacute infectious encephalopathies are extremely resistant to standard decontamination processes. Available data on this aspect mostly originate from studies on the inactivation of agents of scrapie and Creutzfeldt-Jacob disease. The etiological agent of scrapie is highly resistant to temperature change. When exposed to temperatures of up to 80° C. their infectiousness is only slightly reduced; higher temperatures however markedly reduce infectiousness (Hunter et al., J. Gen. Microbiol. 37:251, 1964). A small quantity of infectious "virus" sometimes persists when suspensions of infected material are heated to 100° C. for 1 hour or to 118° C. for 10 minutes.

Recently, the need was felt to renew standards of sterilizing these infectious agents under high steam pressure in autoclaves. The current standards governing autoclaving in the United States for the decontamination of Creutzfeldt-Jacob disease involve treatment at 132° C. for 1 hour (Rosenberg et al., Annals of Neurology 19:75, 1986), and is based on studies carried out on brain homogenates containing scrapie or Creutzfeldt-Jacob agents (Brown et al., J. of Infectious Diseases 153:1145, 1986). In Britain the current standard of autoclaving for decontamination from Creutzfeldt-Jacob disease involves treatment in an autoclave at 134°–138° C. for 18 minutes, on the basis of some studies including one by Kimberlin (Kimberlin et al., Journal of Neurological Sciences 59:355, 1983). Unfortunately, the bovine spongiform encephalopathy agents are very resistant even to common chemical treatments, as well as physical ones. Solvents such as benzene, hexane, petrol and trichloroethylene have been used as extraction solvents, but little is known of their effects on infectivity. Only a small quantity of data is available on the chemical inactivation of infective agents, mainly because studies require large numbers of animals and long observation times. Concentrations of 0.3%–2.5% of sodium hypochlorite greatly reduced infectivity in the biological assays used, but often did not completely eliminate it (Walker et al., Am. J. Publ. Health 73:661, 1983). Data regarding treatment with up to 0.25N sodium hydroxide are very variable; at concentrations of over 1N it appears however to be the most efficacious chemical agent of all those studied. Treatment with 6M–8M urea was also reported to be highly variable.

The results of the studies on decontamination thus show that, although most of the infectivity is quickly destroyed by many of the different physical and chemical processes, the existence of small subpopulations of resistant infectious agents makes sterilization of contaminated materials extremely difficult in practice.

Once BSE had been identified as a "scrapie-like" disease, important questions began to be asked on epidemiological and analytical levels, the latter in particular being aimed at identifying the agent associable with infectivity. However, all efforts so far made to identify nucleic acids associated with the etiological agent have been unfruitful. The only component isolated, which is associated unequivocally with the infective action, is a sialoglycoprotein called scrapie prion protein ($Prp^{Sc}$).

Genetic studies conducted on this protein subsequently provided some surprising information. Some DNA probes synthesized according to the N terminal sequence of the protein have made it possible to show the presence of a chromosome gene in individual copy that exhibits the same restriction pattern both in the brains of healthy animals as in the brains of infected animals. This gene, which is conserved even in very different species, codes a protein called cellular prion protein ($PrP^C$) with an apparent molecular weight of 33–35.0 kilodaltons (kd), which shows particularly evident differences with respect to the $PrP^{Sc}$:

1) $PrP^C$ is susceptible to protease, while $PrP^{Sc}$ is resistant. In particular, while $PrP^C$ is degraded completely by the enzyme proteinase K, $PrP^{Sc}$ is hydrolyzed at the level of the N terminal for a fragment of about 5 kd and gives rise to a protein called $PrP_{27-30}$. This form copurifies with the infectivity and is the most abundant component that is obtained in the preparations of infective material.

2) Both $PrP^C$ and $PrP^{Sc}$ are membrane proteins, but while the first is solubilized by treatment with detergents, the second tends to polymerize into amyloid fibrous structures. Similar structures (scrapie-associated fibrils, SAF) have been found in infected brains and are peculiar for this type of infection. The resistance of this infective protein to inactivation is unusual: it is sensitive, for example, to treatments with concentrated alkaline solutions or to exposure to temperatures above 120° C. and to their combinations or combinations with different denaturing agents. Consequently, the only diagnostic methods available for unequivocal identification of these spongiform encephalopathies are the verification of the presence of the SAF in the infected cerebral tissues, extraction and immunochemical identification of the protein $PrP_{27-30}$, methodologies applicable only during pathological anatomy.

The SAF have been identified on infected bovine brains, then the homolog of the $PrP^{Sc}$ was isolated and showed reactivity with a serum obtained against mouse SAF. Further, the N terminal sequence of the first 12 amino acids showed 100% homology with the $PrP^{Sc}$ of sheep and a difference from that of the mouse, hamster and man by a single insertion of glycine. As soon as it was established that BSE is a "scrapie-like" disease, some important questions arose at the epidemiological and analytic level, the latter particularly devoted to identifying the protein associable with infectivity.

The unexpected cropping up of BSE and all the aspects still to be explained on these neurological disorders have caused a necessary consideration to be given to the problem, especially by those involved in the preparation of products that derive from bovine material.

It could, in fact, not be enough to use, for obtaining compounds or their mixtures of pharmaceutical interest, raw material certified for food use. Consequently, it is necessary to develop the process of production of the products in question by using extraction methodologies that guarantee the elimination of the protein associated with infectivity and the infectivity itself. It is obvious that the process of extraction of the infectively active fraction should, at the same time, preserve the biological activity of the active principles desired as final product.

The other potentially dangerous protein at the level of these preparations for man is the myelinic basic protein (MBP).

It is a protein that in man and most vertebrates has a molecular weight (MW) of about 19.5 kd. It is present in three molecular forms in human myelin and in six in that of the mouse, coding by a single gene located on chromosome 18 and it constitutes about 30% of the total myelinic protein. Its exact topographical location is not yet certain. It has been observed in the cytoplasm of oligodendrocytes only at the moment of myelinization. A protein considered identical is present in the peripheral nervous system (protein P1), and the ability of peripheral myelin to induce experimental allergic encephalomyelitis (EAE) in laboratory animals is due to it.

Not all the molecule of MBP is encephalitogenic but only a portion that varies from species to species: in the rabbit the encephalitogenic portion is amino acid fragment 64–73, in the Lewis rat 71–85, in the guinea pig 113–121, in the SJL/J mouse 89–169. The EAE is a typical cell-dependent autoimmune disease; indeed, it is transferable from one animal to another by infusion of the sensitized T lymphocytes and not by infusion of serum. In this case, the disease is supported by transfused lymphocytes and not those of the recipient. Another cell-dependent autoimmune form is allergic experimental neuritis (EAN). It too can be induced in all species of higher vertebrates by inoculation of crude homogenate of peripheral myelin in complete Freund's adjuvant. It is considered that the antigen mainly responsible for this autoimmunization is protein P2, with an MW of 12.0 kd, present in the peripheral nervous system.

Another contaminant to be considered in these preparations is bovine genomic DNA. The possibility of being able to produce, by recombinant DNA technology, biologically active proteins, which can be used as pharmaceutical agents, has made it necessary to analyze the final products for the presence of DNA residues, belonging to the cell where the desired protein is expressed. The presence of DNA fragments in pharmaceutical preparations to be used in man poses the problem of the danger of an incorporation in the genome of these fragments with a possible uncontrolled transfer of genetic type information. Even though it is not yet possible to obtain gangliosides by recombinant DNA technology, it is necessary to apply this type of control analytical technology to extraction products that use raw material of animal origin.

Finally, the gangliosides to be used in vitro and in vivo studies should be free from other compounds such as asialogangliosides and glycocerebrosides. These substances, if present in high concentrations, can have important immunological implications and can also lead to erroneous experimental considerations.

The sudden onset of BSE and all the other aspects still to be clarified on these neurological disorders have caused necessary consideration to be given to the problem, especially by those involved in the preparation of products deriving from bovine material.

Earlier processes for preparation of gangliosides, such as cited above, required the product to be pharmaceutically acceptable, free from those biological contaminants which were known at the time to be potentially damaging to the health. But clearly, the subsequent onset of the aforesaid pathology in adult cattle has made it necessary to obtain an active principle which, without losing the aforesaid therapeutic properties, is characterized by the assured absence of non-conventional viral agents, to be achieved by the use of specific processes to guarantee the inactivation of these non-conventional viral agents and the complete elimination of infectivity, and to use specific methodologies by which to identify such agents. Indeed, it may not be enough to use raw material which has been certified as suitable for consumption, to obtain compounds or mixtures of the same for pharmaceutical purposes. Obviously, the onset of BSE must be assessed by taking into account its biological action in vivo, which must be considered as an example of verification of the various phases of the process, but not as a summary of the same. This analysis of the biological action in vivo is necessary since scientists are not yet in agreement over associating the infection with certain proteins such as $PrP_{27-30}$. Clearly, the extraction process which eliminates infectious activity must at the same time leave the biological activity of the active principle intact, since this is essential for its therapeutic use. (Ad hoc working party on biotechnology/pharmacy: Validation of virus removal and inactivation process. Commission of the European Communities, March 1990). Scientific research has produced, on the one hand, methods which guarantee suitable mixtures of gangliosides or their single fractions to be obtained in forms free from protein, chemical and biological contaminants, and on the other hand, methods with demonstrated efficacy in destroying infectivity associated with slow viruses, but no method is known by which it is possible to obtain, also on an industrial scale, the similarly unknown result of a product, as desired, pure, pharmacologically active product, free from infectivity associable with pathogenic agents definable as slow viruses.

DETAILED DESCRIPTION OF THE INVENTION

The aim of the present invention is to supply a product characterized by the absence of slow viruses obtained by an advantageous process which can be applied to industrial production, and a process, the innovativeness of which is founded on the suitable sequencing of its various extraction phases. This process which eliminates during its various phases infectious contaminants associable with slow viruses such as bovine spongiform encephalopathy, allows the activity of the mixture, which represents the therapeutic activity of the product itself, to remain unaltered. The product deriving from this process is constituted by a definite mixture of gangliosides or single fractions obtained from bovine brain or parts of the same.

The process according to the present invention is composed, for the above reasons, of the following main phases:
a) subjecting bovine brain tissue to lipid elimination in acetone;
b) suspension of an acetone precipitate in an mixture of methylene chloride/methanol/sodium hydroxide at a temperature of between 30° C. and 35° C. for at least 3 hours to partition hydrophobic and hydrophilic substances;
c) solubilization of the precipitate with water/chloroform/methanol and sodium hydroxide (pH 12) by heating to between about 38° C. and 43° C. for 4 to 8 hours;
d) solubilization of the precipitate with sodium hydroxide 1N at room temperature for at least one hour; and
e) neutralization and dialysis of the solution containing the ganglioside mixture through a membrane with a MW cutoff of 10 kd.

Hereafter, for the purpose of illustration and not limitation, examples are described of preparations made from infected bovine brains where the spongiform encephalopathy form was encountered or from protein raw materials obtained from uninfected bovine brains to which are added constant amounts of infected material from the 263K scrapie strain.

Materials and Methods

The bovine brains used in the process for extraction of the ganglioside mixture showed, on histological analysis, fibrils typical to tissues belonging to materials from animals with the infection.

Preparation Examples

EXAMPLE 1

Figure 1:
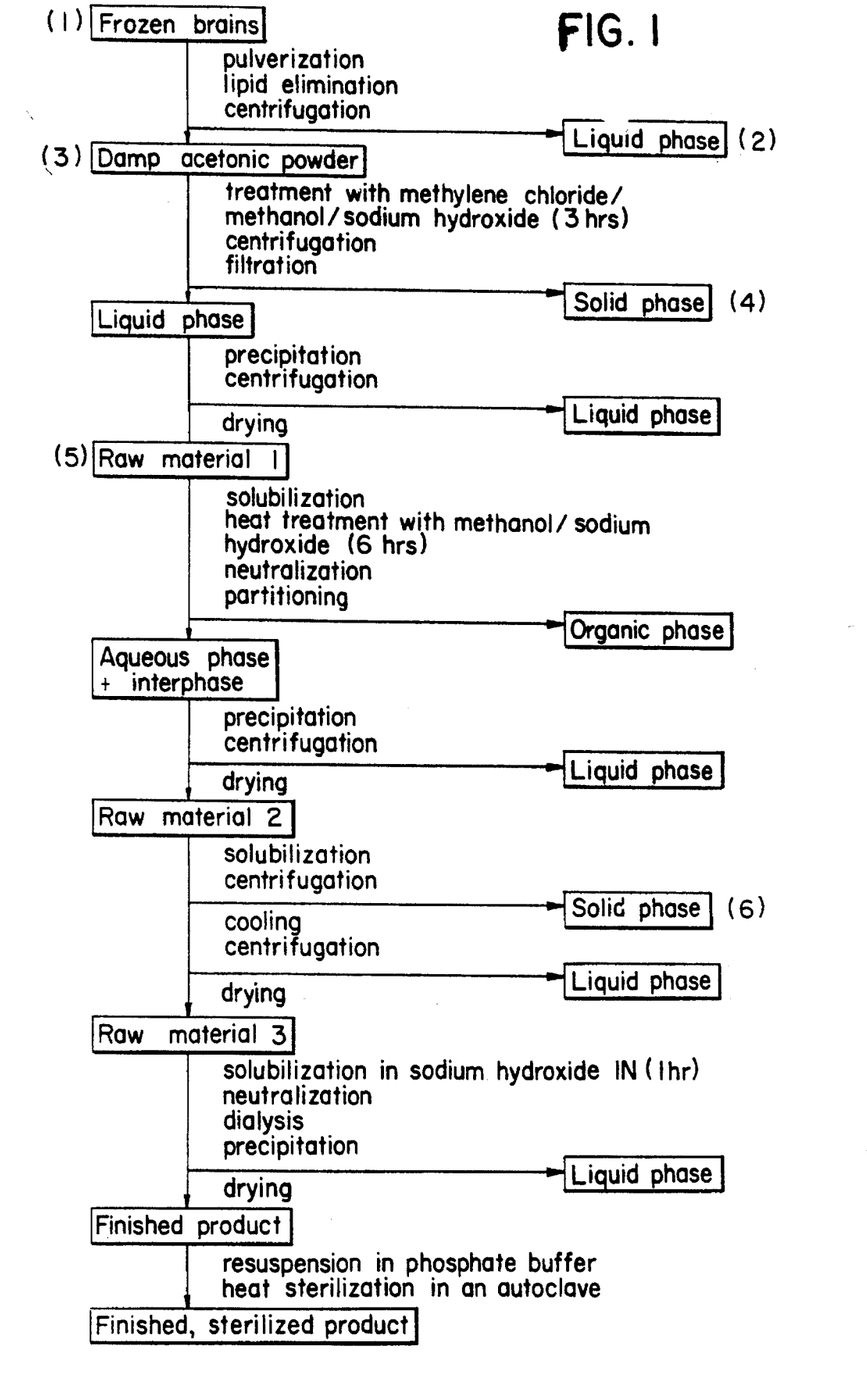
FIG. 1 is a schematic diagram of the process of the invention.

A diagram of the preparation process is shown in FIG. 1.

1000 grams of infected bovine brain, ground and suspended in distilled water, were left in contact with 300 to 600 ml acetone (ratio 1:5 weight/volume) for about 3 hours at room temperature under stirring. The solution was then centrifuged at 6000×g at a temperature of between 7° C. and 4° C. until precipitation was complete. The solvent was then eliminated and 180–350 ml of a mixture of methylene chloride/methanol/sodium hydroxide was added to the wet powder placed in a suitable glass container and was left again under magnetic stirring for at least three hours at a temperature of between 30° C. and 35° C. It was finally left to cool and then was centrifuged for 20 minutes at 6000×g at +10° C. The liquid phase was filtered through a filtering funnel at a temperature of +4° C. A suitable amount of calcium chloride and acetone was added to the liquid, it was left under stirring for about 30 minutes and centrifuged at 6000×g at +10° C. The precipitate (raw material 1) was finally allowed to dry overnight and then for 5 hours in a high vacuum. Recovered raw material 1 was resuspended in 10 to 18 ml of a mixture of water/chloroform/methanol. The pH was adjusted to around 12 with 5N NaOH. The whole was heated to between 38° and 43° C. from about 4 to 8 hours and left under stirring. At the end, after being allowed to cool, it was neutralized with 6N HCl and the required amount of water/n-butanol/chloroform was added. It was stirred for 15 to 30 minutes and left to stand for between 2 and 4 hours. Finally, the lower organic phase was discarded, acetone and sodium chloride were added to the remaining aqueous phases, they were stirred for about 30 minutes and centrifuged for 20 minutes at 6000×g at +15° C. (raw material 2).

The product was dried in a high vacuum, resuspended in 6 to 15 ml absolute methanol and then kept hot for about 2 hours while stirring the solution from time to time. The suspension was then quickly centrifuged at 6000×g and the supernatant was placed in a freezer for about 2 hours. The opalescent white solution was then centrifuged at 0° C. at 600×g and the precipitate was dried in a high vacuum. The product was gathered in 1N sodium hydroxide and left in contact with the solution for at least 1 hour at room temperature. Finally, the pH of the suspension was brought to an approximate pH value of 9 and dialysed with a membrane having a MW cutoff of 10 kd against a suitable volume of distilled water. A suitable amount of sodium chloride and acetone was added and centrifuged at +5° C. at 6000×g, and then dried in a high vacuum (finished product). The sample was taken up in 10 mM of phosphate buffer pH 7.2 and sterilized at +121° C. for 30 minutes (finished, sterilized product).

Evaluation of Process

As explained above, an important aspect of the process of the invention is the provision of a ganglioside product which is free of undesirable contaminants, particularly free of non-conventional viruses. To evaluate the process, samples at various stages of the procedure were tested for possible contamination.

The procedure and results for biological/clinical testing are as follows:

Biological Test for Scrapie

The animals used in these experiments were Golden Syrian hamsters (LVG/Lak). Tests for infection were carried out on groups of four weaned, female animals which had received intracerebral (i.c.) inoculation with 0.05 ml of the samples diluted ten times in sterile PBS. The intracerebral inoculations were effected by trained staff using disposable glass syringes with 26G, ⅜-inch sterile needles.

The final, sterilized product, concentrated 20 times, was used entirely as follows:

4.0 ml injected intracerebrally in 40 animals.

3.0 ml diluted 1:20 and injected, undiluted, intracerebrally in 50 animals and i.p. in 22 animals. The volume injected i.p. was 2.5 ml.

The animals were examined twice a week or more, for a period of 12 months, for the onset of the characteristic neurological, clinical symptoms. The onset of early symptoms in each animal was recorded, and the animals were sacrificed when the disease was well established. Their brains were divided in two halves, one fixed in 10% formalin and the other preserved at −70° C. Pathological diagnosis was made in all animals which died of suspect causes and those which had shown signs of neurological disorders. At the end of the observation time, all surviving animals were sacrificed and pathological assessment was made of their brains.

The infective titer was calculated at the "final end point" according to the method of Reed and Munch, and is expressed as log $LD_{50}$/ml.

The samples tested were the following, utilizing names for the products as noted in FIG. 1:

All samples were resuspended in sterile PBS in the following volumes, so calculated as to ensure a homogeneous titer per volume compared to the 16.7% w/v homogenate as the starting material:

| Powdered brain | ml 2.0 | brain homogenate 16.7% w/v, undiluted |
|---|---|---|
| Raw material 1 | ml 5.4 | undiluted |
| Raw material 2 | ml 9.7 | undiluted |
| Finished product | ml 14.4 | undiluted |
| Finished, sterile product | ml 7.0 | concentrated 20 times |

Results of the biological/clinical tests are set forth in Table 1.

TABLE 1

BIOLOGICAL ASSAY AND CLINICAL ASSESSMENT
(inactivation experiment)

| SAMPLE DILUTION | 16.7% BRAIN HOMOGENATE | SICK | RAW MATERIAL 1 | SICK | RAW MATERIAL 2 | SICK | FINAL PRODUCT | SICK | FINAL STERILIZED PRODUCT | SICK |
|---|---|---|---|---|---|---|---|---|---|---|
| 20-fold conc. | | | | | | | | | 40-20232 | 0/28 |
| Undiluted | | | 4-20216 | 0/3 | 4-20222 | 0/3 | 4-20227 | 0/4 | 50-20233 (ic) | 0/35 |
| $10^{-1}$ | | | 4-20217 | 1/3 | 4-20223 | 0/0 | 4-20228 | 0/4 | | |
| $10^{-2}$ | | | 4-20218 | 0/1 | 4-20224 | 0/4 | 4-20229 | 0/4 | | |
| $10^{-3}$ | | | 4-20219 | 0/3 | 4-20225 | 0/4 | 4-20230 | 0/4 | | |
| $10^{-4}$ | 4-20210 | 4/4 | 4-20220 | 0/2 | 4-20226 | 0/4 | 4-20231 | 0/2 | | |
| $10^{-5}$ | 4-20211 | 4/4 | 4-20221 | 0/3 | | | | | | |
| $10^{-6}$ | 4-20212 | 3/3 | | | | | | | | |
| $10^{-7}$ | 4-20213 | 3/3 | | | | | | | | |
| $10^{-8}$ | 4-20214 | 1/4 | | | | | | | | |
| $10^{-9}$ | 4-20215 | 0/1 | | | | | | | | |
| TOTAL | 24 | 15/19 | 24 | 1/15 | 20 | 0/15 | 20 | 0/18 | 90 | 0/63 |

All animals which had shown clinical signs of scrapie and all animals still surviving at the end of the one-year monitoring time were included into the study. Animals which had been put down because of accidents and/or poor health, and those which had died of causes unrelated to scrapie or which had been killed for meat, not having shown any clinical signs of the disease, were not included. The "sample" column reports the number of animals injected at the beginning of the experiment and the cage number, which distinguishes the different samples and dilutions. The "sick" column reports the number of animals which showed clinical signs of scrapie/number of animals injected minus number of animals which died of causes unrelated to scrapie.

Additional Evaluations

Determination of scrapie protein PrP is made by polyclonal antibodies specific for the purified protein analog from murine brain and which cross-react with the scrapie PrP of bovine origin. The Western Blot method was used for the determination. The presence of the scrapie PrP was evaluated by comparison with the standards for proteins with various molecular weights.

Determination of the MBP protein was made by polyclonal antibodies specific for the purified protein analog from bovine cerebral tissue. The method used for the determination is that of the Western Blot. The presence of the MBP was evaluated by comparison with the standard of proteins with various molecular weights.

Determination of the bovine genomic DNA was performed by the DOT BLOT technique on samples taken at different phases of the processing according to the method known to those skilled in the art. To consider the sample valid, the presence of spots should not be noted in the depositions of the heterologous DNA. The absence of spots in the samples examined in the radioautography shows the absence of bovine genomic DNA.

Figure 2:
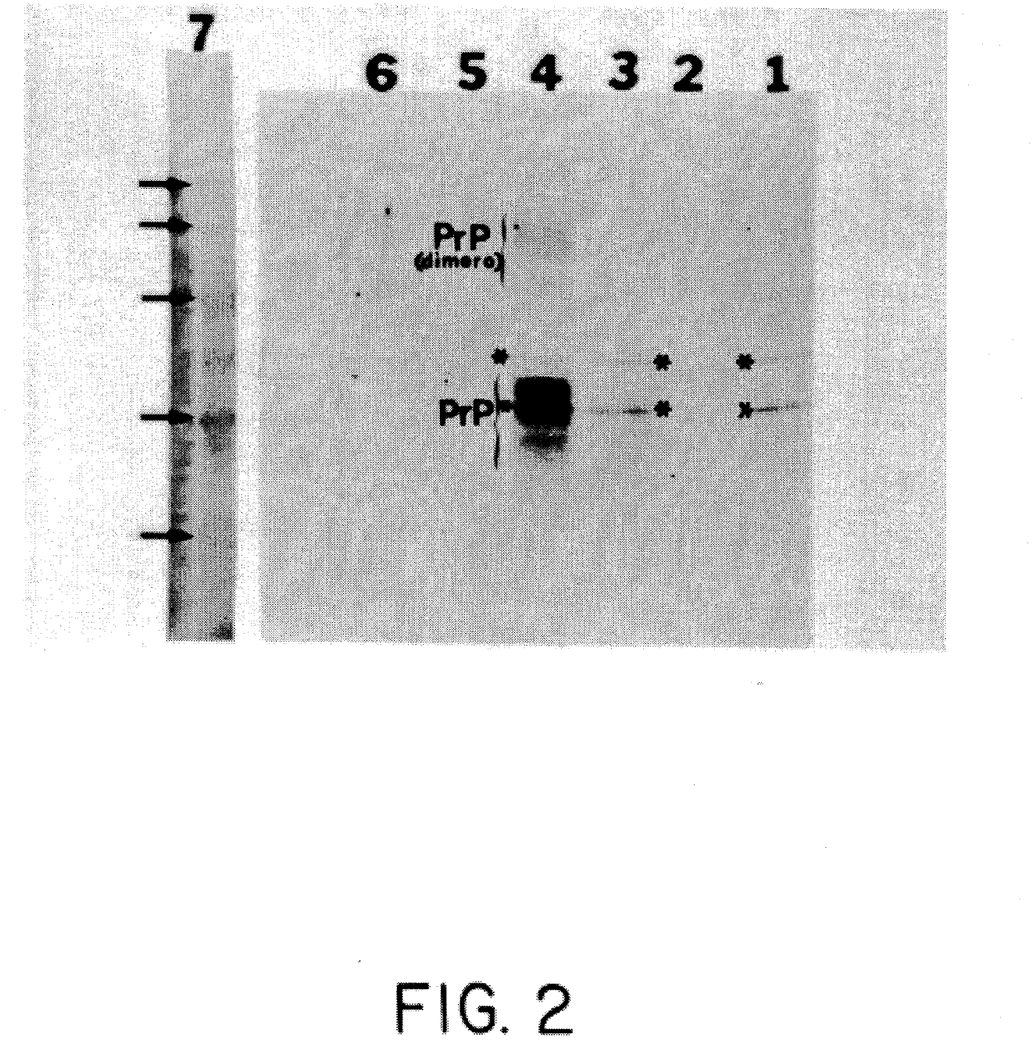
FIG. 2 is a photograph showing results obtained by the use of anti-$Prp_{27-30}$ antibodies by the Western Blot technique to analyze some samples taken from intermediate passages of the process of the invention.
Figure 3:
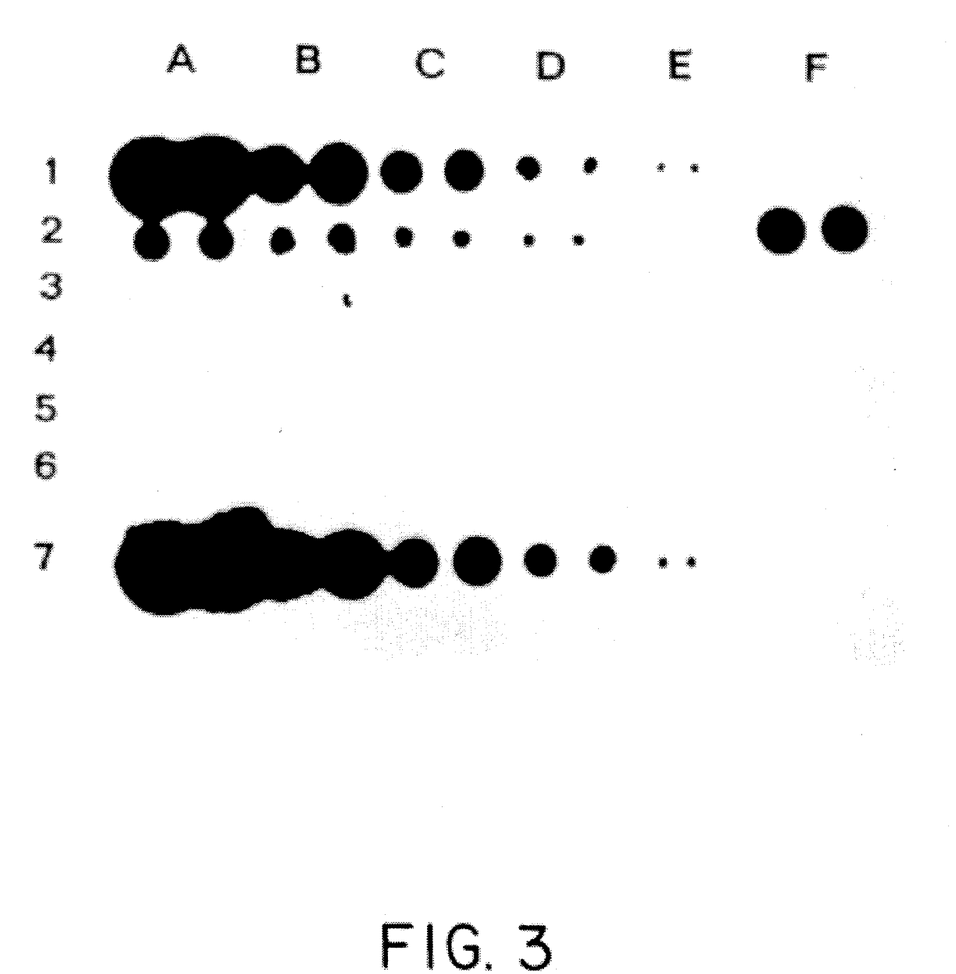
FIG. 3 is a photograph showing results of the analysis of bovine genomic DNA on some samples taken from various passages of the process of the invention.
Figure 4:
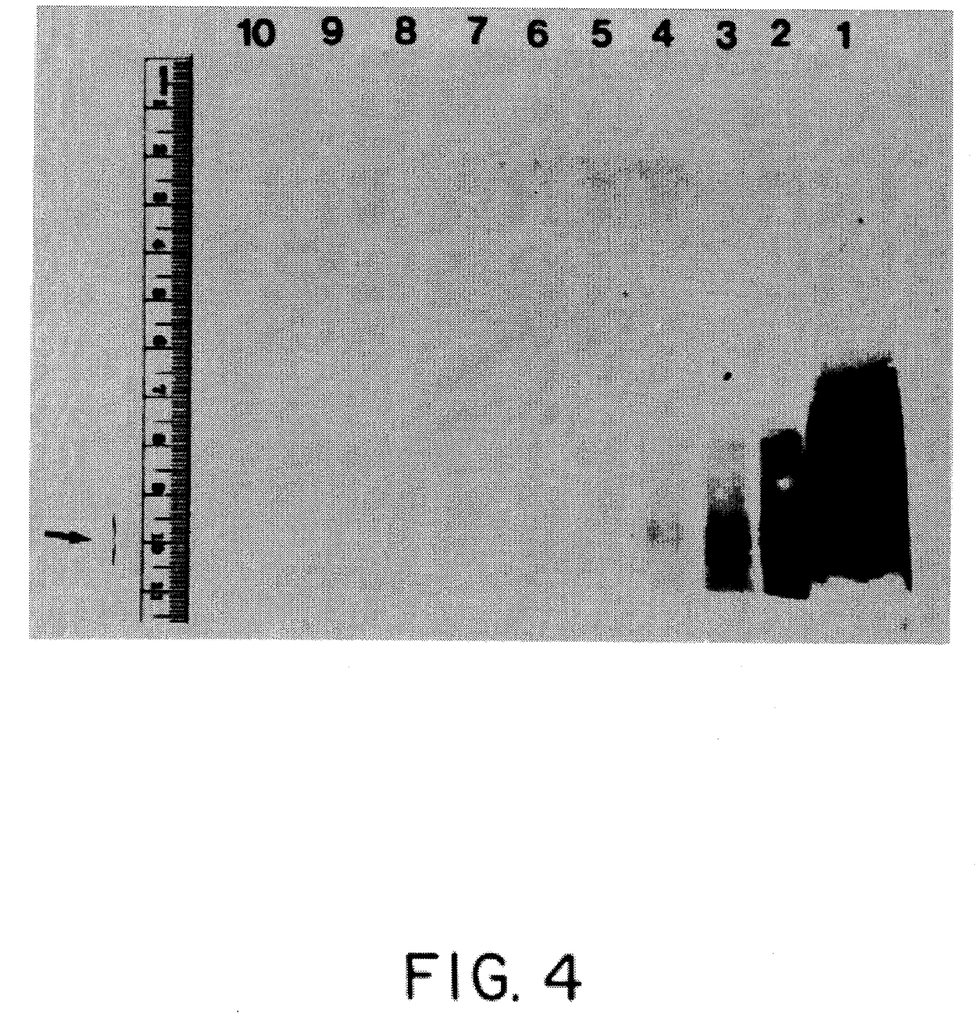
FIG. 4 is a photograph of the results obtained by the use of anti-MBP antibodies in the Western Blot technique to analyze some samples taken from intermediate passages of the process of the invention.
Figure 5:
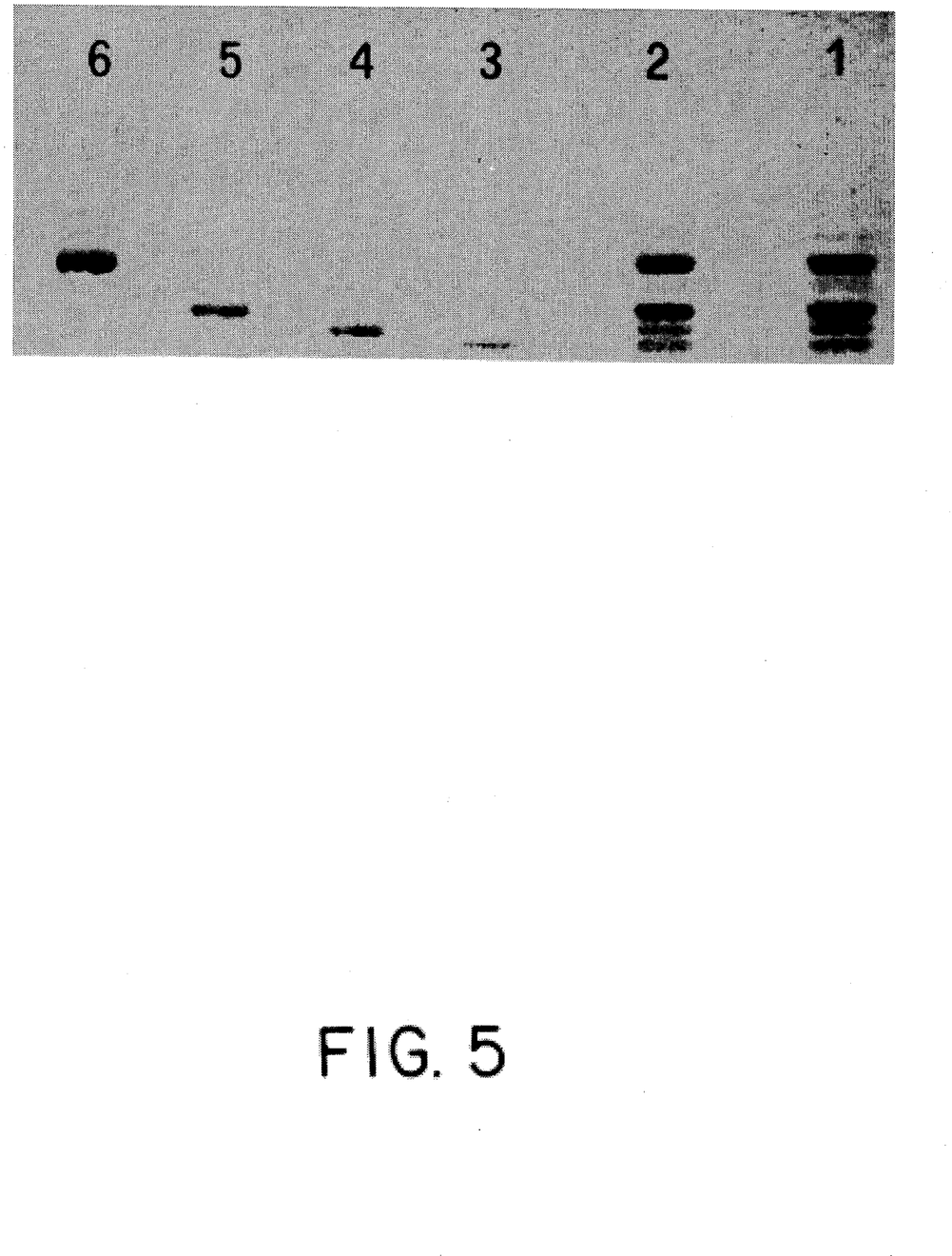
FIG. 5 is a photograph of the results of silica gel chromatography analysis of the ganglioside mixture prepared according to the process of the invention.
Figure 6:
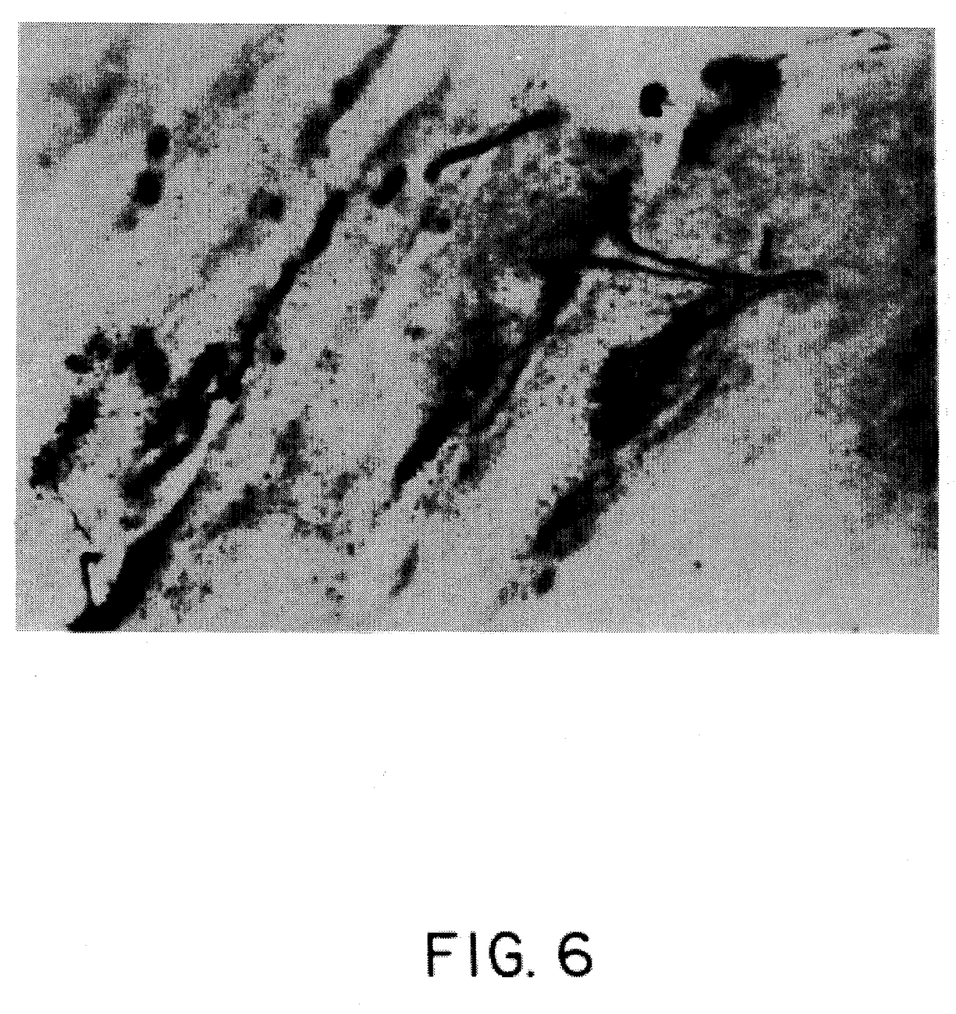
FIG. 6 is a photograph showing the biological activity of the ganglioside mixture prepared according to the invention.
Figure 7:
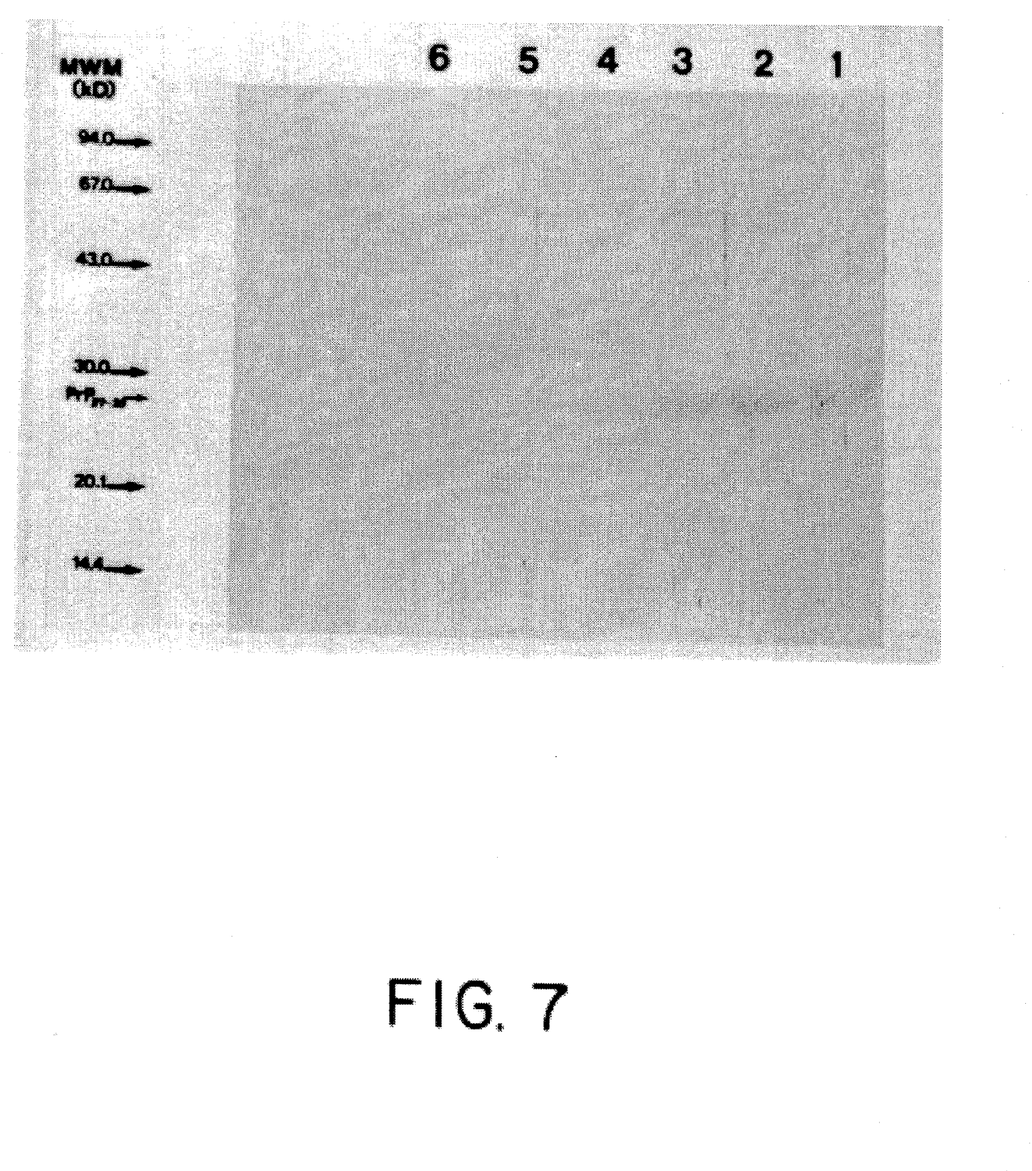
FIG. 7 is a photograph showing the results of immunochemical analysis with anti-$PrP_{27-30}$ antibodies of samples taken from intermediate passages of the process of the invention.

FIG. 2 shows the results determined by immunochemical analysis with anti-$PrP_{27-30}$ antibodies of samples coming from some intermediate stages of the ganglioside preparation and purification process. The number codes of the analyzed samples corresponds to the numbers in parentheses given in the purification diagram of FIG. 1.

Lane 1: code 1 sample
Lane 2: code 2 sample
Lane 3: code 3 sample
Lane 4: code 4 sample
Lane 5: code 5 sample
Lane 6: finished product
Lane 7: protein with standard MW (downward the kd's are as follows: 97.4, 66.2, 45.0, 31.0, 21.5)

Bands with asterisk refer to nonspecific cross-reactions attributable to the system of amplification of the assay.

FIG. 3 shows the analysis of bovine genomic DNA by the DOT BLOT technique on samples taken from various passages of the process.

Intersection of letters with numbers indicates:

Standard curves

1A–7A bovine DNA (1 mg)

1B–7B bovine DNA (1 ng)

1C–7C bovine DNA (100 pg)

1D–7D bovine DNA (10 pg)

1E–7E bovine DNA (1 pg)

1F–7F bovine DNA (0 pg)

Samples examined

2A–2F code 1 sample 2B code 2 sample 2C code 3 sample 2D code 5 sample 2E code 6 sample 3A crude 3 sample 3B finished product 3C finished, sterilized product The points of the standard curve and the analyzed samples are given in duplicate.

FIG. 4 reports results of immunochemical analysis with anti-MBP antibodies of samples coming from some intermediate passages of the preparation and purification process. The code of the samples corresponds to the numerals indicated in the purification diagram of FIG. 1.

Lane 1: code 1 sample

Lane 2: code 2 sample

Lane 3: code 3 sample

Lane 4: code 4 sample

Lane 5: code 5 sample (raw material 1)

Lane 6: crude 2 sample

Lane 7: code 6 sample

Lane 8: crude 3 code sample

Lane 9: finished product

Lane 10: finished, sterilized product

The various forms of MBP recognized by the polyclonal antibodies used are in parentheses.

FIG. 5 shows the results of chromatography on silica gel of the following samples (also according to the process outlined in FIG. 1):

Lane 1: finished, sterilized product

Lane 2: finished product

Lane 3: standard of trisialoganglioside $GT_{1b}$

Lane 4: standard of disialoganglioside $GD_{1b}$

Lane 5: standard of disialoganglioside $GD_{1a}$

Lane 6: standard of monosialoganglioside $GM_1$

FIG. 6 is an example photograph to show the biological activity of the ganglioside mixture prepared according to the inventions (the arrows indicate the sprouting) on a peripheral nerve.

FIG. 7 shows results of immunochemical analysis with anti-$PrP_{27-30}$ antibodies of samples taken from some intermediate passages of ganglioside purification and preparation processes. The code of the analyzed samples corresponds to the numerals indicated in the purification diagram of FIG. 1.

Lane 1: solution of raw material 1 to which has been added 1.5 micrograms/ml of $PrP_{27-30}$ Lane 2: raw material 2 code sample Lane 3: code 6 sample Lane 4: raw material 3 code sample Lane 5: finished product Lane 6: finished, sterilized product

EXAMPLE 2

Preparation of a clarified homogenate from infected brains

Four hamster brains, infected with the 263K scrapie strain, corresponding to a net weight of 3.9 g, were homogenized in 10 ml of distilled water. The volume was then brought to 15.5 ml in order to obtain a homogenate of 25% w/v. The suspension was centrifuged for 40 minutes at 1800×g at 4° C.: 7.5 ml of supernatant were recovered, divided into aliquots and kept at −70° C. until use.

Preparation of the samples 5 ml of the infected homogenate, 120 ml of methanol/methylene chloride and 0.71 ml of 5.7N sodium hydroxide were added to 10 g of acetone powder of bovine brains. This addition was made in order to keep the total volume of the aqueous phase in the solvent constant and to obtain the most suitable operative conditions. The final titer of the starting solution was 1% w/v. The suspension was magnetically stirred for 3 hours at a temperature of 33° C. It was then cooled and centrifuged for 20 minutes at 6000×g at 10° C.

The liquid phase was filtered through a Gooch funnel (pore size No. 3) at a temperature of +4° C. to avoid evaporation of the solvents; at the end of this stage 78 ml of liquid phase were recovered. A 2 ml aliquot was retained for biological assays. To both aliquots an appropriate volume of calcium chloride and acetone was added, and after being magnetically stirred for about 30 minutes at room temperature, the samples were centrifuged for 10 minutes at 6000×g at 10° C. The precipitate (raw material 1) was dried in a hood overnight and then for 2 hours in high vacuum. One aliquot was kept at −70° for the purposes of biological assay.

The 925 mg of raw material 1 recovered from the reaction container were resuspended in 18.5 ml of a mixture of chloroform/methanol/water and 0.74 ml of the homogenate to obtain a titer of 1% w/v. The pH was adjusted to an approximate value of 12 (assessed with a litmus paper) adding 5N NaOH, and the mixture was magnetically stirred at 40° C. for 6 hours. After cooling to room temperature, the solution was neutralized with 6N HCl and an aliquot of 250 µl was retained for the purposes of biological assay.

Both aliquots were treated with a suitable volume of n-butanol/chloroform/water and after stirring for 15 minutes they were left to stand for 4 hours. Finally, the lower organic phases were discarded. To the remaining aqueous phases were added sodium chloride and acetone and, after magnetic stirring at room temperature for about 30 minutes, they were centrifuged for 10 minutes at 6000×g at 15° C. (raw material 2).

This product was dried in high vacuum and the aliquot set aside for biological assay was preserved at −70° C. The remaining material was resuspended in 6.5 ml of absolute methanol and left at 50° C. for 2 hours and stirred from time to time. The suspension was quickly centrifuged at 6000×g and the supernatant placed in a freezer at −20° C. for 2 hours.

The cold, white, opalescent solution was then centrifuged at 0° C. at 6000×g for 5 minutes and the precipitate was dried in high vacuum. The yield at this point was 6 mg of product. This was then resuspended in 500 µl of sodium hydroxide, 460 µl of distilled water and 40 µl of homogenate and left in contact with this solution for 1 hour at room temperature. Finally, the pH of the suspension was adjusted to an approximate value of 9 (assessed with litmus paper) and dialysed with a membrane having a MW cut off of 10 kd for 4 hours against 20000 volumes of distilled water. The final volume after dialysis was 980 µl. It was divided into two aliquots of 500 µl and 480 µl respectively; to the first was added the required volume of sodium chloride and acetone and it was centrifuged for 10 minutes at 6000×g at 5° C. This sample was dried in high vacuum (final product).

To the second aliquot was added 20 µl of homogenate and 50 µl of PBS 10x and it was sterilized at 121° C. for 30 minutes (final, sterilized product).

Evaluation of the Process

As described above for Example 1, samples taken from the various stages of the process were tested for potential presence of contaminants.

The samples tested and results are as follows:

All of the samples were gathered in sterile PBS in the following volumes, so calculated as to ensure a homogeneous titer per volume compared to the 1% homogenate w/v as the starting material:

| | | |
|---|---|---|
| Brain homogenate 25% w/v diluted to 1% | | undiluted susp. |
| Raw material 1 | ml 3.2 | undiluted |
| Raw material 2 | ml 1.0 | undiluted |
| Finished product | ml 0.5 | undiluted |
| Finished, sterilized product | ml 0.5 | undiluted |

Table 2 reports the results obtained by biological assay.

TABLE 2

BIOLOGICAL ASSAY SCHEME AND CLINICAL EVALUTATION
(spiking experiment)

| SAMPLE DILUTION | 1% BRAIN HOMO- GENATE | SICK | RAW MATERIAL 1 | SICK | RAW MATERIAL 2 | SICK | FINAL PRODUCT | SICK | FINAL STERILIZED PRODUCT | SICK |
|---|---|---|---|---|---|---|---|---|---|---|
| Undiluted | | | 4-20450 | 0/4 | 4-20456 | 0/3 | 4-20462 | 2/3 | 4-20468 | 4/4 |
| $10^{-1}$ | | | 4-20451 | 0/4 | 4-20457 | 0/3 | 4-20463 | 0/3 | 4-20469 | 4/4 |
| $10^{-2}$ | | | 4-20452 | 0/3 | 4-20458 | 0/2 | 4-20464 | 0/3 | 4-20470 | 3/3 |
| $10^{-3}$ | | | 4-20453 | 0/4 | 4-20459 | 0/3 | 4-20465 | 0/3 | 4-20471 | 0/2 |
| $10^{-4}$ | 4-20444 | 4/4 | 4-20454 | 0/3 | 4-20460 | 0/3 | 4-20466 | 0/0 | 4-20472 | 0/3 |
| $10^{-5}$ | 4-20445 | 4/4 | 4-20455 | 0/1 | 4-20461 | 0/3 | 4-20467 | 0/3 | 4-20473 | 0/3 |
| $10^{-6}$ | 4-20446 | 2/3 | | | | | | | | |
| $10^{-7}$ | 4-20447 | 0/0 | | | | | | | | |
| $10^{-8}$ | 4-20448 | 0/3 | | | | | | | | |
| $10^{-9}$ | 4-20449 | 0/2 | | | | | | | | |
| TOTAL | 24 | 10/16 | 24 | 0/19 | 24 | 0/17 | 24 | 2/15 | 24 | 11/19 |

All animals which had shown clinical signs of scrapie and all animals still surviving at the end of the one-year monitoring time were included into the study. Animals which had been put down because of accidents and/or poor health, and those which had died of causes unrelated to scrapie or which had been killed for meat, not having shown any clinical signs of the disease, were not included. The "sample" column reports the number of animals injected at the beginning of the experiment and the cage number, which distinguishes the different samples and dilutions. The "sick" column reports the number of animals which showed clinical signs of scrapie/number of animals injected minus number of animals which died of causes unrelated to scrapie.

EXAMPLE 3

Biological Activity of Ganglioside Mixture

A series of experiments was carried out in vitro in order to verify whether the ganglioside mixture (obtained according to the aforesaid process) possessed any biological activity predictive of therapeutic application to treat pathologies of the peripheral nervous system (PNS) and of the central nervous system (CNS). In particular, the activity of gangliosides was tested in vitro to assess neurite formation in cultures of neuroblastoma cells ($N_2A$). These cells, as described in literature (Denis—Donini et al., Neuronal Development, part II, 323:348—Academic Press, NY 1980; Leon et al., Dev. Neurosci. 5:108, 1982) may induce, in certain conditions, the expression of various functions characteristic of mature neurons, thus allowing a qualitative and quantitative analysis of biochemical parameters correlated with each stage of development.

Therefore, the assessments made in this model (% of cells with neurite formation, neurite length and relative branching) are valid instruments when investigating the possible therapeutic application of a drug in functional recovery of the nervous system.

Materials and Methods

Cell cultures

Mouse C 1300 cells, clone $N_2A$, supplied by America Cell Type Collection (Bethesda, Md.), were plated at a concentration of 10,000 cells per well (24-castor) in the presence of Dulbecco's modified Eagle medium (DMEM) containing P/G (100 U.penicillin/ml) and 10% fetal calf serum (FCS from Seromed, batch 4-CO4).

The next day the culture medium was changed with the same volume of fresh medium containing gangliosides (see further). The cultures were kept at 37° C. in 5% $CO_2$ in a humidified atmosphere (Haerus incubator). The cultures were then fixed with 2% glutaraldehyde at the appointed time (24 hours later).

Preparation of the test solutions of the product

The ganglioside mixture (3 different batches, Nos. 1-2-3) was dissolved in chloroform/methanol 2:1, dried in a stream of nitrogen, resuspended in DMEM+P/G+ 10% FCS until the desired concentrations were reached.

Concentrations examined: $1 \times 10^{-4}M$; $5 \times 10^{-5}M$ and $1 \times 10^{-5}M$.

Four different experiments were carried out as follows:

3 experiments to assess the effect of ganglioside mixture (batch Nos. 1 and 2) at a concentration of $1 \times 10^{-4}M$ 1 experiment to assess the dose-response effect of different concentrations ($1 \times 10^{-4}$, $5 \times 10^{-5}$ and $1 \times 10^{-5}M$) of the ganglioside mixture under examination (batch No. 3).

Process

The medium was drawn off the wells and substituted with 350 µl of DMEM+P/G+10% FCS±product under examination (at the aforesaid concentrations).

The control cultures were treated in the same way, without the addition of the ganglioside mixture. The cultures were then kept in an incubator for 24 hours, after which the cells were fixed with 2% glutaraldehyde and observed under a microscope.

Parameters

Morphological examination set out to assess:

the percentage (%) of cells with neurites length of neurites and relative branching.

Results

As reported in Table 3, it is clear that the products under examination are efficacious ($1 \times 10^{-4}M$) in inducing the formation of neurites in $N_2A$ cells.

The effect of the ganglioside mixture is dose-dependent with maximum efficacy at the dose of $1 \times 10^{-4}M$ (Tab. 4).

TABLE 3

Effect of ganglioside mixture (batches 1, 2) on neurite formation in mouse neuroblastoma $N_2A$ cells. All products were added to the cells at a final concentration of $1 \times 10^{-4}M$, morphological evaluations were made 24 hours later.

| | % of cells with neurites | | |
|---|---|---|---|
| Product | 1st exp. | 2nd exp. | 3rd exp. |
| Control | 2 ± 1 | 1 ± 1 | 2 ± 2 |
| GA (1) | 29 ± 6 | 27 ± 6 | 24 ± 5 |
| GA (2) | 25 ± 4 | 25 ± 2 | 25 ± 5 |

(batch No in brackets)

TABLE 4

Effect of different concentrations of ganglioside mixture (batch 3) on neurite formation in mouse neuroblastoma $N_2A$ cells; dose-effect response.

| Product | Concentration | % cells with neurites |
|---|---|---|
| Control | | 3 ± 2 |
| GA (3) | $1 \times 10^{-4}$ | 35 ± 6 |
| GA (3) | $5 \times 10^{-5}$ | 17 ± 5 |
| GA (3) | $1 \times 10^{-5}$ | 4 ± 2 |

(batch No. in brackets)

Figure 8:
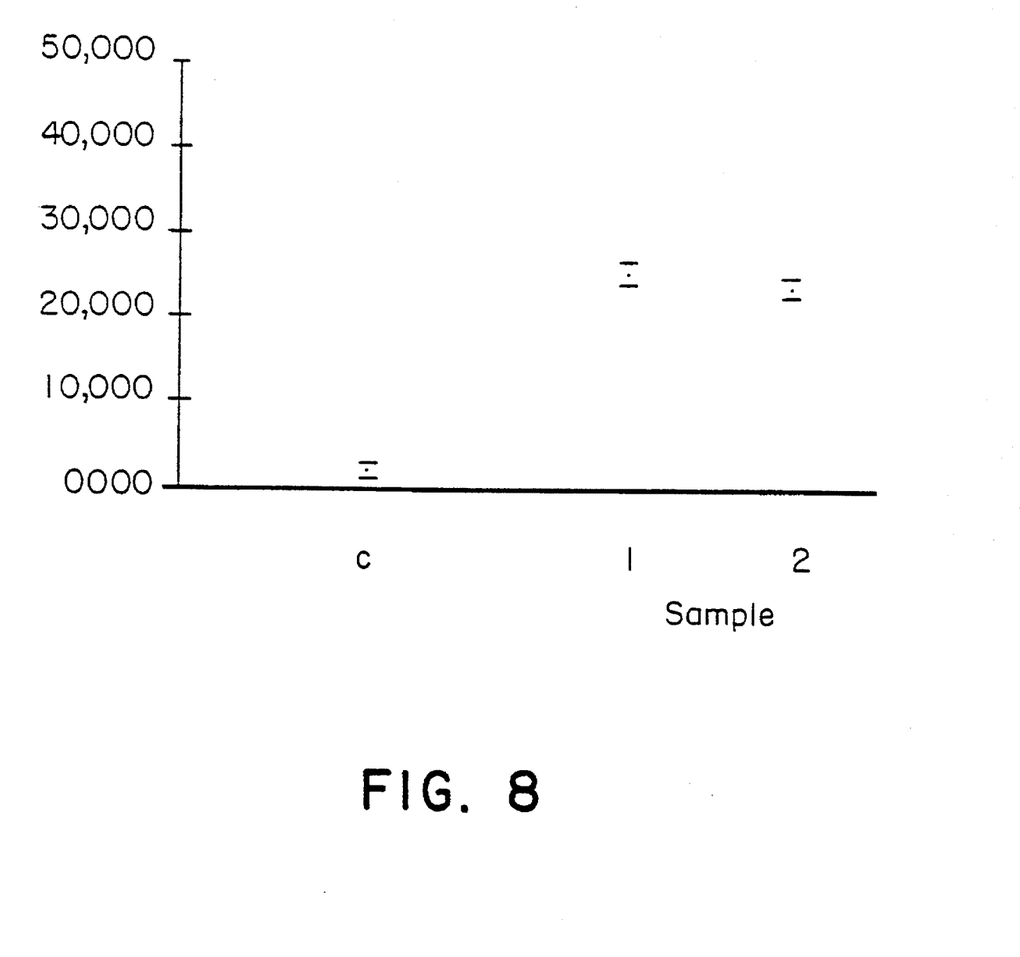
FIG. 8 is a plot of the statistical assessment of data for the in vitro activity of the preparation according to the invention.

Statistical assessment of data on the biological activity in vitro indicates that there is no significant difference between the various batches of ganglioside mixture (FIG. 8).

FIG. 8

Moreover, morphological assessment of the neurites shows that the cells treated with ganglioside mixture present long, notably branched neurites (i.e. marked branching).

Conclusions

The aforesaid observations, therefore, affirm that the ganglioside mixture under examination has a biological activity, indeed, the product obtained, by a process which guarantees its particular characteristics, can induce neurite formation in $N_2A$ cells. This fact indicates that the product is efficacious in repair phenomena of the peripheral and central nervous systems. The mixture of gangliosides, obtained as described and free from contaminants associated with potentially dangerous non-conventional viruses, can also be used for the preparation of individual components or the ganglioside mixture, such as monosialoganglioside $GM_1$.

In view of the pharmacological properties described above, the ganglioside mixture can be generally used as a drug in numerous pathologies (with various etiopathogenic causes) in both the peripheral and central nervous systems. Specific conditions which can be treated are: retrobulbar optic neuritis, paralysis of the oculomotor nerves, trigeminal neuralgia, paralysis of the facial nerve and Bell's palsy, Garcin's syndrome, radiculitis, traumatic lesions of the peripheral nerves, diabetic and alcoholic polyneuritis, obstetrical paralysis, paralytic sciatica, motor neuron diseases, amyotrophic lateral sclerosis, myelopathic muscular atrophy, progressive bulbar paralysis, myasthenia gravis and Lambert Eaton's syndrome, muscular dystrophy, impairments in synaptic nerve transmission in the CNS and PNS, consciousness deficiencies such as confusion, concussion, thrombosis, cerebral embolism, cerebral and spinal trauma.

Administration is usually by injection, intramuscular, subcutaneous or intravenous, or by transdermal, pulmonary or oral routes, preferably in suitably buffered aqueous solutions. Safe storage of the pharmaceutical can be ensured by preparing it in the form of vials containing solutions of the product, possibly together with other auxiliary ingredients, as indicated in the examples of pharmaceutical preparations reported hereafter. For the therapeutic, or possibly also preventive application by the aforesaid parenteral route, the dosage varies preferably between 10 mg and 100 mg/day of active substance.

For purely descriptive and not limitative purposes, the following are examples of pharmaceutical compositions made according to the present invention.

EXAMPLE 1

One vial is composed as follows:

| Active component | |
|---|---|
| Gangliosides as sodium salts<br>monosialotetrahexosylganglioside (GM$_1$)<br>disialotetrahexosylganglioside (GD$_{1a}$)<br>disialotetrahexosylganglioside (GD$_{1b}$)<br>trisialotetrahexosylganglioside (GT$_{1b}$) | 10.0 mg |
| Other components | |
| dibasic sodium phosphate 12 H$_2$O | 6.0 mg |
| monobasic sodium phosphate 2 H$_2$O | 0.5 mg |
| sodium chloride | 16.0 mg |
| water for injection to | 2.0 ml |

EXAMPLE 2

One vial is composed as follows:

| Active component | |
|---|---|
| Gangliosides as sodium salts<br>monosialotetrahexosylganglioside (GM$_1$)<br>disialotetrahexosylganglioside (GD$_{1a}$)<br>disialotetrahexosylganglioside (GD$_{1b}$)<br>trisialotetrahexosylganglioside (GT$_{1b}$) | 20.0 mg |
| Other components | |
| dibasic sodium phosphate 12 H$_2$O | 6.0 mg |
| monobasic sodium phosphate 2 H$_2$O | 0.5 mg |
| sodium chloride | 16.0 mg |
| water for injection to | 2.0 ml |

EXAMPLE 3

One vial is composed as follows:

| Active component | |
|---|---|
| Gangliosides as sodium salts<br>monosialotetrahexosylganglioside (GM$_1$)<br>disialotetrahexosylganglioside (GD$_{1a}$)<br>disialotetrahexosylganglioside (GD$_{1b}$)<br>trisialotetrahexosylganglioside (GT$_{1b}$) | 100.0 mg |
| Other components | |
| dibasic sodium phosphate 12 H$_2$O | 12.0 mg |
| monobasic sodium phosphate 2 H$_2$O | 1.0 mg |
| sodium chloride | 32.0 mg |
| water for injection to | 4.0 ml |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A process for the preparation of a mixture of gangliosides free of slow viral infectivity without altering its biological and pharmacological characteristics which comprises:

a) subjecting ganglioside-containing tissue to lipid elimination with acetone to produce an acetone precipitate;

b) suspending said acetone precipitate at a temperature of 30°–35° C. for at least 3 hours in a first solvent mixture of methylene chloride and methanol which comprises sodium hydroxide in an amount sufficient to eliminate slow viral activity and maintain the liquid as one single phase, and is capable of separating hydrophobic substances from hydrophilic substances;

c) filtering the mixture obtained from step (b) to obtain a first liquid phase;

d) subjecting said first liquid phase to precipitation to obtain a first raw material;

e) solubilizing said first raw material in water/chloroform/methanol which comprises sodium hydroxide and subjecting the solubilized first raw material to heating at about 38° to 43° C. for about 4 to 8 hours at a pH of about 12 and allowing the mixture to cool to room temperature;

f) neutralizing the mixture and subjecting said solubilized first raw material to partitioning in a second solvent mixture capable of partitioning hydrophobic substances from hydrophilic substances;

g) separating said partitioning mixture to remove an organic phase and retain an aqueous phase;

h) subjecting said aqueous phase to precipitation to produce a second raw material;

i) solubilizing said second raw material in methanol which is kept hot and thereafter subjected to cooling to produce a third raw material;

j) solubilizing said third raw material in 1N NaOH for at least one hour at room temperature;

k) neutralizing said solubilized third raw material; and l) subjecting said neutralized solubilized third raw material to dialysis through a membrane with a molecular weight cut off of about 10 kd to produce a ganglioside mixture.

2. A process according to claim 1, wherein said precipitation of said first raw material is conducted by adding calcium chloride and acetone.

3. A process according to claim 1, wherein said heating of said first raw material is conducted at about 40° C. for about 4 to 8 hours.

4. A process according to claim 1, wherein said first raw material is solubilized in a mixture of water, chloroform and methanol, and, after said heating, then said second solvent mixture is added comprised of a mixture of water, chloroform and n-butanol.

5. A process according to claim 1, wherein precipitation of said second raw material is conducted by adding acetone and sodium chloride.

6. A process according to claim 1, wherein said ganglioside-containing tissue is bovine brain tissue.

7. A process according to claim 6, wherein said produced ganglioside mixture is subjected to drying to produce a finished product ganglioside mixture.

8. A process according to claim 7, wherein said finished product ganglioside product is suspended in buffer and sterilized to produce a finished, sterilized ganglioside mixture product.

9. A process for the preparation of a mixture of gangliosides free of slow vital infectivity without altering its biological and pharmacological characteristics which comprises:

a) subjecting bovine brain tissue to lipid elimination with acetone to produce an acetone precipitate;

b) suspending said acetone precipitate at a temperature of 30°–35° C. for at least 3 hours in a first solvent mixture of methylene chloride, methanol and sodium hydroxide in an amount sufficient to eliminate slow viral activity and maintain the liquid as one single phase;

c) filtering said first solvent mixture containing said acetone precipitate to obtain a first liquid phase;

d) subjecting said first liquid phase to precipitation by addition of calcium chloride to obtain a first raw material;

e) solubilizing said first raw material in water, chloroform and methanol, and subjecting the solubilized first raw material to heating in a solvent which comprises sodium hydroxide at a pH of about 12 and a temperature of about 38° to 43° C. for at least 4 to 8 hours;

f) subjecting said heated solubilized first raw material to a second partitioning in a mixture of water, n-butanol and chloroform;

g) separating said second partitioning mixture to remove an organic phase and retain an aqueous phase;

h) subjecting said aqueous phase to precipitation by the addition of acetone and sodium chloride and centrifugation to produce a second raw material;

i) solubilizing and heating said second raw material in methanol;

j) centrifuging said solubilized and heated second raw material to produce a supernatant;

k) cooling said supernatant to produce a third raw material;

l) solubilizing said third raw material in sodium hydroxide for about one hour;

m) neutralizing said solubilized third raw material; and n) subjecting said neutralized solubilized third raw material to dialysis through a membrane with a molecular weight cut off of about 10 kd to produce a ganglioside mixture.

10. A process according to claim 9, wherein said solubilization of said third raw material is in 1N sodium hydroxide.

11. A process according to claim 10, wherein said produced ganglioside mixture is subjected to drying to produce a finished product ganglioside mixture.

12. A process according to claim 11, wherein said finished product ganglioside product is suspended in buffer and sterilized to produce a finished, sterilized ganglioside mixture product.

13. A process according to claim 1 or 9, which further comprises separating the ganglioside mixture into individual ganglioside components.

14. A process according to claim 13, wherein the ganglioside $GM_1$ is separated from the ganglioside mixture.

15. A process for the preparation of a mixture of gangliosides free of slow viral infectivity without altering its biological and pharmacological characteristics which comprises:

a) subjecting bovine brain tissue to lipid elimination with acetone to produce an acetone precipitate;

b) suspending said acetone precipitate at a temperature 30°–35° C. for at least 3 hours in a first solvent mixture of methylene chloride, methanol and sodium hydroxide in an amount sufficient to eliminate slow viral activity and maintain the liquid as one single phase;

c) filtering said first solvent mixture containing said acetone precipitate to obtain a first liquid phase;

d) subjecting said first liquid phase to precipitation by addition of calcium chloride to obtain a first raw material;

e) solubilizing said first raw material in water, chloroform and methanol, and subjecting the solubilized first raw material to heating in a mixture of methanol and sodium hydroxide at a pH of about 12 and a temperature of about 38° to 43° C. for at least 4 to 8 hours;

f) subjecting said heated solubilized first raw material to a second partitioning in a mixture of water, n-butanol and chloroform;

g) separating said second partitioning mixture to remove an organic phase and retain an aqueous phase;

h) subjecting said aqueous phase to precipitation by the addition of acetone and sodium chloride and centrifugation to produce a second raw material;

i) solubilizing and heating said second raw material in methanol;

j) centrifuging said solubilized and heated second raw material to produce a supernatant;

k) cooling said supernatant to produce a third raw material;

l) solubilizing said third raw material in about one hour;

m) neutralizing said solubilized third raw material; and n) subjecting said neutralized solubilized third raw material to dialysis through a membrane with a molecular weight cut off of about 10 kd to produce a ganglioside mixture.

16. A process according to claim 15, wherein said solubilization of said third raw material is in 1N sodium hydroxide.

17. A process according to claim 15, wherein said produced ganglioside mixture is subjected to drying to produce a finished product ganglioside mixture.

18. A process according to claim 17, wherein said finished product ganglioside product is suspended in buffer and sterilized to produce a finished, sterilized ganglioside mixture product.

* * * * *